United States Patent [19]
Schmidt et al.

[11] Patent Number: 6,028,104
[45] Date of Patent: Feb. 22, 2000

[54] USE OF PEROXYGEN COMPOUNDS IN THE CONTROL OF HAIRY WART DISEASE

[75] Inventors: William Schmidt, Woodbury; Deborah Anastasia Ihns, St. Paul, both of Minn.

[73] Assignee: Ecolab Inc., St. Paul, Minn.

[21] Appl. No.: 09/013,560

[22] Filed: Jan. 26, 1998

Related U.S. Application Data

[60] Provisional application No. 60/036,575, Jan. 30, 1997, abandoned.

[51] Int. Cl.$^7$ .................................................... A01N 37/00
[52] U.S. Cl. ........................... 514/557; 514/558; 514/560
[58] Field of Search ..................................... 514/557, 558, 514/560

[56] References Cited

U.S. PATENT DOCUMENTS

| | | | |
|---|---|---|---|
| 4,051,058 | 9/1977 | Bowing et al. | 252/186 |
| 4,051,059 | 9/1977 | Bowing et al. | 252/186 |
| 5,066,497 | 11/1991 | Witkin | 424/616 |
| 5,200,189 | 4/1993 | Oakes et al. | 424/405 |
| 5,900,256 | 4/1999 | Scovill, Jr. et al. | 424/616 |

FOREIGN PATENT DOCUMENTS

| | | |
|---|---|---|
| 0 228 137 | 7/1987 | European Pat. Off. . |
| 31 33 425 | 3/1983 | Germany . |
| 98-205404 | 9/1997 | Russian Federation . |

OTHER PUBLICATIONS

Blowey, R., "Practical Approach to the Treatment of Foot Problems", *The Bovine Practitioner*, 0(30):49–50 (May 1996).

Journal of Plant Diseases and Protection, Doz. Dr. E. Donaubauer, Wien et al., 89 vol. 1982, pp. 282–290. An English translation is provided.

Enzymes in Pathogenesis, by D. Subramanian, Supplement to the Proceedings of the Indian Academy of Sciences, vol. LXIX, Section B, pp. 133–141. 1969.

*Primary Examiner*—Russell Travers
*Attorney, Agent, or Firm*—Merchant & Gould P.C.

[57] ABSTRACT

A method of preventing growth of hairy warts and preventing hairy wart disease in dairy cattle by applying to a potentially infected area of the cattle, e.g. hooves, a solution comprising a peroxycarboxylic acid, e.g. of $C_2$–$C_{18}$ carbon atoms or mixtures thereof, particularly peracetic acid, is described.

12 Claims, No Drawings

USE OF PEROXYGEN COMPOUNDS IN THE CONTROL OF HAIRY WART DISEASE

This Application claims benefit of Provisional application Ser. No. 60/036,575 Jan. 30, 1997 now abandoned.

FIELD OF INVENTION

The invention relates to the prophylactic treatment of foot disease in dairy cattle. More specifically, the invention relates to the use of peroxycarboxylic acids in the control of organisms which cause hairy wart disease in dairy cattle.

BACKGROUND OF THE INVENTION

Hairy wart disease, also called Papillomatus Digital Dermatitis (PDD), Infectious Bovine Interdigital Dermatitis (IDD), Digital Dermatitis (DD), or Stable Foot Rot (SFR) is an infectious disease transmitted among animals. The effects of the disease are lameness, loss of weight, decline of general well-being; in the case of dairy cattle, a loss of milk production and the resulting economic loss to the dairy farmer. Interventive surgery may be required to protect the life of the animal.

The disease is thought to be caused by *Fusobacterium mecrophorum, Dichelobacter nodosus,* and *Bacteroides melaninogenicus.* All are anaerobic spirochetes, live in the intestinal track, and are reported to live in the manure/soil for up to ten months.

Present treatments include foot baths containing copper sulfate, zinc sulfate, formaldehyde, tetracycline and mixtures containing sodium hydroxide and sodium hypochlorite. Only tetracycline has been reported to be efficacious and generally when combined with some surgical techniques including a bandage of the infected area that has been treated with tetracycline. There is thus a need for a product that would be more effective in controlling hairy wart disease than presently available products, especially since the disease is becoming one of the biggest issues facing the dairy producer due to reports of the disease spreading throughout dairy herds in the United States.

The use of peroxycarboxylic acids in antimicrobial compositions has been reported, for example, as sanitizing agents, antimicrobial agents, and disinfectants. Particularly, peroxyacetic acid has been used in poultry farm applications as a general disinfectant where control of bacteria and virus is a critical factor. The use of peroxyacetic acid directly on animals for treating infectious diseases has not been reported.

SUMMARY OF THE INVENTION

The invention is related to the novel use of peroxycarboxylic acid compounds on hairy warts and/or related foot diseases in dairy cattle. A peroxycarboxylic acid product included in the present invention has been found to be effective in preventive programs, i.e., prophylactic treatment of animals.

The preventive program, i.e. prophylactic treatment, employs a foot bath in which all of the animals of the herd are exposed to the solution on a daily basis. Alternatively, the animals of the herd may be treated on a daily basis by spraying or foaming the product on the potentially infected areas. The product employs a prophylactically effective amount of peroxycarboxylic acid. Recommended doses use 0.5–10 ounces, preferably 0.5–3 ounces, of a concentrate per gallon of diluent, e.g. water. More preferably, 1 ounce per 1.5 gallons is used.

As an alternative, direct treatment of the infected animals involves spraying a therapeutically effective amount of peroxycarboxylic acid in a diluent. Recommended dosages include 1–10 ounces of concentrate per gallon of diluent. A resulting solution is directly sprayed on the infected areas for a period of 3–10 days. Concentrations up to full strength can be used in severe cases.

Accordingly, the present invention in its first aspect is a method of controlling hairy wart disease in dairy cattle comprising applying daily to said cattle a prophylactically effective amount of an antimicrobial concentrate composition comprising a peroxycarboxylic acid, and a diluent.

DETAILED DESCRIPTION

The process for preventing hairy wart disease in dairy cattle is carried out by applying a solution containing peroxycarboxylic acid(s). The peroxycarboxylic(s) acid is included in an antimicrobial concentrate composition which may also contain the corresponding precursor carboxylic acid and hydrogen peroxide and the balance being water. This concentrate prior to application to the dairy cattle is diluted with a diluent, preferably water, which then is sprayed, foamed or otherwise applied onto the hooves of the dairy cattle or other potentially infected areas of the dairy cattle for prevention. An alternate preventive method is using the solution in a foot bath for the dairy cattle herd.

Antimicrobial Concentrate Composition

The concentrate composition includes an equilibrium mixture of peroxycarboxylic acid(s), their corresponding carboxylic acid(s), hydrogen peroxide and water. The concentrate may also include other ingredients such as stabilizers, couplers, etc. as mentioned below.

Among the above constituents in the antimicrobial concentrate composition the invention comprises a carboxylic acid. Generally, carboxylic acids have the formula R-COOH wherein the R may represent any number of different groups including aliphatic groups, alicyclic groups, aromatic groups, heterocyclic groups, all of which may be saturated or unsaturated as well as substituted or unsubstituted. Carboxylic acids also occur having one, two, three, or more carboxyl groups.

Carboxylic acids have a tendency to acidify aqueous compositions. In acid systems, they may also exhibit antimicrobial activity.

The peroxycarboxylic acid constituent within the present composition functions as the antimicrobial agent. Moreover, the peroxycarboxylic acid constituent within the invention as well as the parent carboxylic acid maintain the composition at an acidic pH.

Percarboxylic acids generally have the formula $R(CO_3H)_n$, where R may represent any number of different groups including aliphatic groups, alicyclic groups, aromatic groups, heterocyclic groups, all of which may be saturated or unsaturated as well as substituted or unsubstituted. Thus, R may be, for example, an alkyl, arylalkyl, cycloalkyl, aromatic or heterocyclic group, and n is one, two, or three, and named by prefixing the parent acid with per or peroxy.

While peroxycarboxylic acids are less chemically stable than their corresponding carboxylic acids, their stability generally increases with increasing molecular weight. Decomposition of these acids may generally proceed by free radical and nonradical paths, by photodecomposition or radical-induced decomposition, by hydrolysis or dissociation or by the action of metal ions or complexes. Peroxycarboxylic acids may be made by the direct, acid catalyzed equilibrium action of 10–98 wt. % hydrogen peroxide with the carboxylic acid, by autoxidation or perhydrolysis of aldehydes, or from carboxylic acid halides, or carboxylic anhydrides with hydrogen, sodium peroxide, or other in-situ sources of hydrogen peroxide.

Peroxycarboxylic acids useful in this invention include $C_2$–$C_{18}$ peroxycarboxylic acids such as, for example, peracetic acid, perpropionic acid, perbutyric acid, perhexanoic acid, perheptanoic acid, peroctanoic acid, pernonanoic acid, perdecanoic acid, perbenzoic acid, perglycolic acid, perglutaric acid, persuccinic acid, perlactic acid, percitric acid, perlauric acid, peradipic acid, permalic acid, perfumaric acid, pertartaric acid or mixtures thereof. These peroxycarboxylic acids have been found to provide good antimicrobial action with good stability in aqueous solutions.

In addition to peracetic, peroctanoic and perdecanoic, particularly preferred percarboxylic acids include perpropionic, perbutyric, perglycolic, perlactic and percitric acids.

The antimicrobial concentrate composition may also use a mixture of peroxycarboxylic acids. Preferred is a combination of peracetic acid with other percarboxylic acids, preferably, those named above and particularly, peroctanoic acid. This combination of peroxycarboxylic acids has been found to provide preferred antimicrobial efficacy and stability. Generally, the ratio of peroctanoic acid to peracetic acid may range from about 1:1 to 1:9.

In its most preferred mode, the antimicrobial concentrate composition of the invention uses peracetic acid. Peracetic acid is a peroxycarboxylic acid having the formula:

Generally, peracetic acid is a liquid having an acrid odor at higher concentrations and is freely soluble in water, alcohol, ether, and sulfuric acid. Peracetic acid may be prepared through any number of means known to those of skill in the art including preparation from acetaldehyde and oxygen in the presence of cobalt acetate. A 50% solution of peracetic acid may be obtained by combining acetic anhydride, hydrogen peroxide and sulfuric acid. Other methods of formulation of peracetic acid include those disclosed in U.S. Pat. No. 2,833,813, which is incorporated herein by reference.

Other methods of formulation of peroxycarboxylic acids within the present invention include those described in U.S. Pat. Nos. 4,051,058, 4,051,059, 5,200,189, 5,314,687 and 5,437,868, which are incorporated herein by reference.

Hydrogen Peroxide

The antimicrobial concentrate composition of the invention may also comprise a hydrogen peroxide constituent. Hydrogen peroxide in combination with the peroxycarboxylic acid provides a surprising level of antimicrobial action against microorganisms. Additionally, hydrogen peroxide may provide effervescent action which may irrigate any surface to which it is applied. Hydrogen peroxide works with a mechanical flushing action once applied which further cleans the surface of the area of application. An additional advantage of hydrogen peroxide is the food compatibility of this composition upon use and decomposition. For example, combinations of peracetic acid and hydrogen peroxide result in acetic acid, water, and oxygen upon decomposition all of which are food product compatible.

While many oxidizing agents may be used, hydrogen peroxide is generally preferred for a number of reasons. After application of the $H_2O_2$/peracetic acid germicidal agent, the residue left merely comprises water and an acidic constituent. Deposition of these products on the surface of the area of application such as the legs and hoofs of dairy cattle, will not give rise to adverse effects.

Hydrogen peroxide ($H_2O_2$), has a molecular weight of 34.014 and it is a weakly acidic, clear, colorless liquid. The four atoms are covalently bonded in a non-polar H-O-O-H structure. Generally, hydrogen peroxide has a melting point of −0.41° C., a boiling point of 150.2° C., a density at 25° C. of 1.4425 grams per $cm^3$, and a viscosity of 1.245 centipoise at 20° C.

Generally, the concentration of hydrogen peroxide within the composition used in the process of the invention ranges from about 1 weight percent to about 50 weight percent, preferably from about 3 weight percent to about 40 weight percent, and most preferably from about 5 weight percent to about 30 weight percent.

These concentrations of hydrogen peroxide may be increased or decreased while still remaining within the scope of the invention.

Adjuvants

The antimicrobial composition of the invention may also comprise any number of adjuvants. Specifically, the composition of the invention may comprise stabilizing agents or wetting agents among any number of constituents which may be added to the composition.

Stabilizing agents may be added to the composition of the invention to stabilize the peracid and hydrogen peroxide. Chelating agents or sequestrants generally useful as stabilizing agents in the invention include alkyl diamine polyacetic acid-type chelating agents such as EDTA (ethylene diamine tetraacetic acid and salts, e.g. the tetrasodium salt), acrylic and polyacrylic acid-type stabilizing agents, phosphonic and diphosphonic acids, phosphonate-type chelating agents among others. Preferable sequestrants include phosphonic acids and phosphonate salts including 1-hydroxy ethylidene-1, 1-diphosphonic acid ($CH_3C(PO_3H_2)_2OH$), amino[tri(methylene phosphonic acid)], 2-phosphene butane-1,2, 4-tricarboxylic acid, as well as the alkyl metal salts, ammonium salts, or alkyloyl amine salts, such as mono, di, or tri-ethanolamine salts. The stabilizing agent is used in a concentration ranging from about 0 weight percent to about 20 weight percent of the composition, preferably from about 0.1 weight percent to bout 10 weight percent of the composition, and most preferably from about 0.2 weight percent to 5 weight percent of the composition.

Also useful in the composition of the invention are wetting agents. Wetting agents function to increase the penetration activity of the antimicrobial composition of the invention and include any of those constituents known within the art to lower the surface energy of the composition of the invention.

In addition, wetting agents may help solubilize the fatty and peroxy fatty acids, enhance the formation of foam and increase the storage stability of the concentrate composition.

As a wetting agent, compositions of the invention can include a surfactant hydrotrope coupling agent or solubilizer that permits blending both fatty acids and short chain peroxy fatty acids in aqueous liquids. Functually speaking, suitable couplers which can be employed are non-toxic and retain the fatty acid and the peroxy fatty acid in aqueous solution throughout any use the solution is exposed.

A preferred class of wetting or hydrotropic coupling agent or solubilizer which can be used in the present invention are anionic surfactants of the sulfonate and sulfate type, such as alkyl benzene sulfonates having 6–18 carbon atoms in the alkyl, alkyl sulfates and/or alkane sulfonates (each having 8–22 carbon atoms in the alkyl or alkane group).

The alkyl benzene sulfonates which can be employed, are preferably those which contain an alkyl radical of 6–18 carbon atoms, preferably 8–15 carbon atoms. Instead of the alkyl benzene sulfonates, alkyl sulfates or alkane sulfonates with an alkyl or alkane radical of the chain length of 8–18 carbon atoms can be employed. If desired, mixtures of the above-mentioned anionic surfactants can also be used.

Nonionic surfactants, may also be useful in the present invention, for example those which comprise ethylene oxide moieties, propylene oxide moieties, as well a mixtures thereof, and ethylene oxide-propylene oxide moieties in either heteric or block formation. Additionally useful in the present invention are nonionic surfactants which comprise an alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to alkyl chain where the ethylene oxide and propylene oxide moieties may be in any randomized or ordered pattern and of any specific length. Nonionic surfactants useful in the present invention may also comprise randomized sections of block and heteric ethylene oxide propylene oxide, or ethylene oxide-propylene oxide.

Generally, the concentration of surfactant used in the invention may range from about 0 wt-% to about 5 wt-% of the composition, preferably from about 0 wt-% to about 2 wt-% of the concentrate composition, and most preferably from about 0 wt-% to about 1 wt-% of the composition.

The invention may also contain any number of other constituents as necessitated by the application, which are known to those of skill in the art and which may facilitate the activity of the present invention.

The concentrate composition used in the invention may comprise:

|  | Composition (Wt-%) | | |
| --- | --- | --- | --- |
|  | Useful | Working | Preferred |
| Peroxycarboxylic Acid | 2–25 | 2–20 | 4–20 |
| H$_2$O$_2$ | 1–45 | 5–35 | 7–30 |
| Carboxylic Acid | 1–70 | 3–55 | 5–45 |
| Surfactant | 0–20 | 0–10 | 0–5 |
| Chelating Agent | 0–20 | 0–10 | 0–5 |
| Water | Balance | Balance | Balance |

Generation of Peroxy Acids

The process of the invention may also be initiated through the use of peroxy acid concentrate compositions. In such a case, the peroxycarboxylic acid may either be generated naturally or through the combination of a hydrogen peroxide concentrate together with a carboxylic acid concentrate at the sight of use such as that process which is described in Lokkesmoe et al., U.S. Pat. No. 5,122,538, issued Jun. 16, 1992, which is incorporated herein by reference. In such a case, the composition may be formed from a hydrogen peroxide concentrate comprising varying levels of hydrogen peroxide and stabilizer as shown in the table below.

|  | Concentration (Wt-%) | | |
| --- | --- | --- | --- |
| Constituent | Useful | Working | Preferred |
| Hydrogen Peroxide | 5–70 | 15–70 | 25–60 |
| Stabilizer | 0–10 | 0–5 | 0.1–3 |
| H$_2$O | 20–95 | 25–85 | 37–75 |

When combined with a carboxylic acid, the two concentrates result in a peroxycarboxylic acid. Generally, the carboxylic acid concentrate comprises a carboxylic acid in water as shown in the table found below.

|  | Concentration (Wt-%) | | |
| --- | --- | --- | --- |
| Constituent | Useful | Working | Preferred |
| Carboxylic Acid | 50–100 | 65–100 | 80–100 |
| Water | 0–50 | 0–35 | 0–20 |

Control of Hairy Wart Disease

Direct treatment of pre-existing warts on dairy cattle may be carried out by administering through a spray a concentration of about 1–10 ounces of an antimicrobial concentrate composition as described above per gallon of diluent, e.g. of water, on the infected areas once per day or at each milking for periods of 3–10 days. Alternatively, and especially for severe cases, the antimicrobial concentrate composition may be sprayed, foamed or otherwise applied to the infected area without a diluent. This procedure may then be followed by additional treatments at each milking of about 0.5–3 ounces, preferably 1.5 ounces, of concentrate per gallon of diluent until the wart has been eliminated.

Maintenance/prevention or prophylactic treatment may be carried out by either spraying or using foot baths at concentrations of approximately 0.5–10 ounces of antimicrobial concentrate composition per gallon of diluent. The preferred dosage is 0.5–3 ounces per gallon; more preferred is 1.5 ounces per gallon. When employing foot baths, these are recharged when peroxycarboxylic acid is depleted due to introduction of significant soil (organic and/or inorganic). The foot baths are kept full for all milkings during the day. Spray applications are carried out once per day at each milking depending upon the severity of the problem.

Using the peroxyacetic acid formula concentrate disclosed in Working Example 1, the active POAA concentration in use concentrations is as follows:

| oz. product per gallon water | POAA concentration (ppm) |
| --- | --- |
| 0.5 | 254 |
| 1.0 | 508 |
| 1.5 | 762 |
| 3 | 1524 |
| 10 | 5080 |
| no dilution | 58,000 | using the specific gravity of Product (concentrate)=1.12

$$\text{ppm } POAA = \frac{(\text{oz.}/\text{gal})}{128} \times 1.12 \times 0.058 \times 10^6$$

| For Spraying Warts | |
|---|---|
| useful POAA conc. | 250–60,000 ppm |
| preferred | 500–60,000 ppm |
| most preferred | 1,500–5,000 ppm |

The above methods have been found to be effective in preventive programs for this disease. Thus, for example, using an antimicrobial concentrate composition containing 27.5 wt-% hydrogen peroxide and 5.8 wt-% peroxyacetic acid diluted with water to 0.5 wt-% resulted in a percent reduction of >99.778% bacteria against *Dichelobacter (Bacteroides) nodosus* and >99.999% reduction for *Fusobacterium necrophorum* when tested in vitro. These bacteria are attributed of causing hairy wart disease.

WORKING EXAMPLES

The invention will now be described in more detail by reference to the following examples. The only proper construction of these examples is as non-limiting illustrative examples showing various formulations, stabilities, and applications of the invention.

Working Example 1

A stock solution of concentrate peroxyacetic acid (or "POAA") was prepared for use in the tests described/containing the following components at equilibrium concentration.

| Component | Wt-% |
|---|---|
| Peroxyacetic Acid | 5.8 |
| Hydrogen Peroxide | 27.5 |
| Acetic Acid | 8.0 |
| HEDP[a] | 0.9 |
| LAS[b] | 1.0 |
| H$_2$O | Balance |

[a]. . . HEDP is 1-hydroxyethylidene-1,1-diphosphonic acid (stabilizer) (Monsanto-Dequest ® 2010)
[b]. . . LAS is a linear alkylbenzene sulfonate (anionic surfactant)

The following in vitro test was carried out using the above POAA concentrate.

| TEST ORGANISMS: | CULTURE MEDIUM: |
|---|---|
| *Dichelobacter (Bacteroides) nodosus* (ATCC 27521) | Tryptic Soy Agar with 5% Blood |
| *Fusobacterium necrophorum* (ATCC 27852) | Tryptic Soy Agar with 5% Blood |

The microorganisms used in this study were obtained from the American Type Culture Collection, Rockville, Md.
SUBCULTURE MEDIUM: Tryptic Soy Agar with 5% Blood Agar Plate
STOCK NEUTRALIZER: 0.5% Sodium Thiosulfate
EXPOSURE TIMES: 15 seconds EXPOSURE TEMPERATURE: 25° C.
METHOD: Official Methods of Analysis of the AOAC, Fifteenth Edition, 1990.
GERMICIDE USE-DILUTION The POAA concentrate was prepared according to the directions for intended use of the product. A 0.5% solution was made using 2.5 ml of POAA concentrate and 497.5 ml sterile deionized water. Product was in solution and used the day it was prepared.

BACTERIAL CULTURES

Three (3) Blood Agar Plates were inoculated with *Fusobacterium necrophorum* and 5 Blood Agar Plates were inoculated with *Dichelobacter (Bacteroides) nodosus*. The Blood Agar Plates were incubated in anaerobic atmosphere for 4 days at 35–37° C. The bacterial growth was washed from each Blood Agar Plate using 2 ml phosphate buffer dilution water. For each organism, the growth suspension was aspirated and pooled together in a sterile vessel. The pooled suspension of each organism was vortex mixed and used for testing.

PROCEDURE 99 ml of product at concentration to be tested was added to each of two 250 ml wide mouth erlenmeyer flasks and placed in 25±2° C. waterbath($\geq$20 min).

Similar flasks containing 99 ml sterile phosphate buffer dilution water were prepared to be used for "initial numbers" control. One ml of culture suspension was added to each flask as follows:

a) The flask was whirled, and stopped just before the suspension was added, which created enough residual motion of liquid to prevent pooling of suspension at point of contact with test water.

b) Suspension was added midway between center and edge of surface with tip of pipette slightly immersed in test solution. (Touching pipet to neck or side of flask during addition was avoided.)

Inoculation of Subculture Media

Test Samples 1 ml of exposed culture was added to 9 ml neutralizer blanks exactly 15 seconds after the addition of suspension. After mixing, four 1.0 ml and four 0.1 ml aliquots were transferred to individual Blood agar plates using the spread plate technique. The *Fusobacterium necrophorum* recovery plates were incubated for 3 days at 35–37° C. before enumeration of survivors. The *Dichelobacter (Bacteroides) nodosus* recovery plates were incubated for 6 days at 35–37° C. before enumeration of survivors.

Number Control 1 ml of culture from "initial numbers" flask was added to 99 ml phosphate buffer dilution water (Dilution1). After mixing thoroughly 1 ml of Dilution 1 was transferred to 99 ml phosphate buffer dilution water (Dilution 2). A third dilution was made using 1.0 ml Dilution 2 into 99 ml phosphate buffer dilution water (Dilution 3). Four 1 ml and four 0.1 m. aliquots from Dilution 3 were transferred to individual petri dishes. Fifteen to twenty ml of Blood Agar were added to each plate and agar was cooled to solidify. The plates were inverted and incubated as in test. The initial suspension was enumerated to determine the number of cfu/ml.

| Controls | Dichelobacter (Bacteroides) nodosus | Fusobacterium necrophorum |
|---|---|---|
| a. Neutralizer Control | No growth | No growth |
| b. Phosphate Buffer Dilution Water | No growth | No growth |
| c. Neutralization Confirmation Control (NC) | | |

One ml and 0.1 ml aliquots of the neutralization control samples (9 ml neutralizer blank tube inoculated with 1 ml of the exposed culture) were transferred to Blood Agar Plates. One ml of test organism suspension was added to the NC Blood Agar Plate, as well as on a sterile Blood Agar control plate. The Blood Agar Plates were incubated as in test. The Blood Agar Plates were examined for the presence of colonies on the surface of the agar and compared to the colonies on the surface of the Blood Agar control plate.

*Dichelobacter* (*Bacteroides*) *nodosus*:

Neutralization Inoculum: 1.0 ml *Dichelobacter* (*Bacteroides*) *nodosus* suspension containing TNTC CFU/ml

| SAMPLE ID | MEDIA | 0.1 ML | 1.0 ML |
|---|---|---|---|
| POAA | BAP | TNTC,TNTC | TNTC,TNTC |

The neutralization controls showed growth, eliminating bacteriostasis as a cause of lack of growth in the test system.

*Fusobacterium necroihorum:*

Neutralization Inoculum: 1.0 ml *Fusobacterium necrophorum* suspension containing TNTC CFU/ml

| SAMPLE ID | MEDIA | 0.1 ML | 1.0 ML |
|---|---|---|---|
| POAA | BAP | TNTC,TNTC | TNTC,TNTC |

The neutralization controls showed growth, eliminating bacteriostasis as a cause of lack of growth in the test system.

TNTC=Too Numerous to Count
BAP=Blood Agar Plate
TEST RESULTS:—After 15 second contact time

| *Dichelobacter (bacteroides) nodosus* | |
|---|---|
| No treatment control | 4.5 × 10³ cfu/ml |
| 0.5% Product (290 ppm POAA) | <1 cfu/ml |
| % Reduction | >99.978% |
| *Fusobacterium necrophorum* | |
| No treatment control | 28.3 × 10⁶ cfu/ml |
| 0.5% Product (290 ppm POAA) | <1 cfu/ml |
| % Reduction | >99.999% | cfu/ml=colony forming units per milliliter
Notes: 1) Results are average of two sets of quadruplicate plating. In all cases less than 1 cfu/ml was found in treated samples.

2) Product used: Working Example 1
When diluted to 0.5%, concentration of POAA=290 ppm in use solution.

CALCULATIONS

Calculate the % reduction.

$$1 - \frac{\text{\# } cfu \text{ test}}{\text{\# } cfu \text{ control}} \times 100 = \% \text{ reduction}$$

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method of controlling hairy wart disease in dairy cattle comprising applying daily to said cattle for controlling hairy wart disease a prophylactically effective amount of an antimicrobial concentrate composition comprising a peroxycarboxylic acid, and a diluent.

2. The method of claim 1 wherein said peroxycarboxylic acid comprises peracetic acid.

3. The method of claim 1 wherein said peroxycarboxylic acid comprises a $C_2$–$C_{18}$ percarboxylic acid or a mixture thereof.

4. The method of claim 1 wherein said peroxycarboxylic acid is selected from the group consisting of peracetic, perpropionic, perbutyric, perglycolic, perlactic, percitric, perlauric, peradipic, perhexanoic, perheptanoic, peroctanoic, pernonanoic, perdecanoic, persuccinic, permalic, perfumaric, pertartaric, perglutaric, perbenzoic and mixtures thereof.

5. The method of claim 1, wherein said antimicrobial concentrate composition comprises:

about 2–25 wt-% of a peroxycarboxylic acid;
about 1–45 wt-% of hydrogen peroxide;
about 1–70 wt-% of a corresponding carboxylic acid, and the balance being water.

6. The method of claim 5, wherein said antimicrobial concentrate composition further comprises a chelating agent.

7. The method of claim 5, wherein said antimicrobial concentrate composition further comprises a surfactant.

8. The method of claim 7, wherein said surfactant is an anionic surfactant.

9. The method of claim 1, wherein a daily dose of about 0.5 to 10 ounces of said antimicrobial concentrate composition per gallon of diluent is applied.

10. The method of claim 9, wherein said daily dose is applied to said cattle in a foot bath.

11. The method of claim 9, wherein said daily dose is applied by automated or manual spraying on a potentially infected area of said cattle.

12. The method of claim 9, wherein said daily dose is applied by foaming on a potentially infected area of said cattle.

* * * * *